United States Patent [19]

Thomas et al.

[11] Patent Number: 5,738,684
[45] Date of Patent: Apr. 14, 1998

[54] EXTERNAL BONE FIXATOR

[75] Inventors: Peter Brian Macfarlane Thomas, Hereford; Peter Jan Ogrodnik, Weston; Christopher Ian Moorcroft, Stafford, all of United Kingdom

[73] Assignees: Keele University; Staffordshire University Enterprises Limited, both of United Kingdom

[21] Appl. No.: 643,156

[22] Filed: Apr. 30, 1996

[30] Foreign Application Priority Data

May 1, 1995 [GB] United Kingdom ............... 9508828

[51] Int. Cl.[6] .................................................. A61B 17/56
[52] U.S. Cl. ............................ 606/54; 606/55; 606/57; 606/102
[58] Field of Search ................................ 606/53, 54, 55, 606/57, 58, 59, 105, 102; 403/52, 53, 55, 57, 58, 120, 129, 132, 136, 144

[56] References Cited

U.S. PATENT DOCUMENTS

| D. 156,325 | 12/1949 | De Ment et al. ............... 403/58 |
| 817,785 | 4/1906 | Kritsch ............................ 403/120 |
| 1,633,695 | 6/1927 | Colley ............................. 403/120 |
| 2,438,664 | 3/1948 | Hansberry ....................... 606/59 |
| 3,650,123 | 3/1972 | Sheppard, Jr. ................... 403/57 |
| 3,727,610 | 4/1973 | Riniker ............................ 606/59 |
| 3,976,061 | 8/1976 | Volkov et al. ................... 606/90 |
| 4,308,863 | 1/1982 | Fischer ............................ 606/57 |
| 4,714,076 | 12/1987 | Comte et al. . | |
| 5,122,140 | 6/1992 | Asche et al. . | |
| 5,167,661 | 12/1992 | Wagenknecht ................. 606/59 |
| 5,405,347 | 4/1995 | Lee et al. ....................... 606/54 |
| 5,437,668 | 8/1995 | Aronson et al. ................ 606/54 |
| 5,456,724 | 10/1995 | Yen et al. ....................... 606/102 |

FOREIGN PATENT DOCUMENTS

| 0 011 258 | 5/1980 | European Pat. Off. . |
| 0 458 486A1 | 11/1991 | European Pat. Off. . |
| 2 697 994 | 5/1994 | France . |
| 699300 | 11/1940 | Germany ................ 403/53 |
| 2 283 178 | 5/1995 | United Kingdom . |
| WO 90/07305 | 7/1990 | WIPO . |
| WO 92/02184 | 2/1992 | WIPO . |
| WO 95/04504 | 2/1995 | WIPO . |

*Primary Examiner*—Michael Buiz
*Assistant Examiner*—Julian W. Woo
*Attorney, Agent, or Firm*—Klauber & Jackson

[57] ABSTRACT

There is described an external fixator for use in the treatment of a fractured bone having a first bone fragment and a second bone fragment which external fixator comprises:

a first movable element and;

a second movable element, wherein the first movable element is movably mounted in the fixator so as to be capable of angular motion in one plane, and the second movable element is movably mounted in the fixator so as to be capable of angular motion in another plane, with the plane in which the second element moves being substantially orthogonal to the plane in which the first element moves, and the first and second movable elements are coupled together in such a way as to allow simultaneous angular movement of the external fixator in the two substantially orthogonal planes. There is also described a bone fixation system for use in the treatment of a fractured bone, which fixation system is provided with a data logging device which is capable of sensing and storing data relating to the frequency of occurrence of an event associated with at least one physical characteristic of the fixation system.

23 Claims, 7 Drawing Sheets

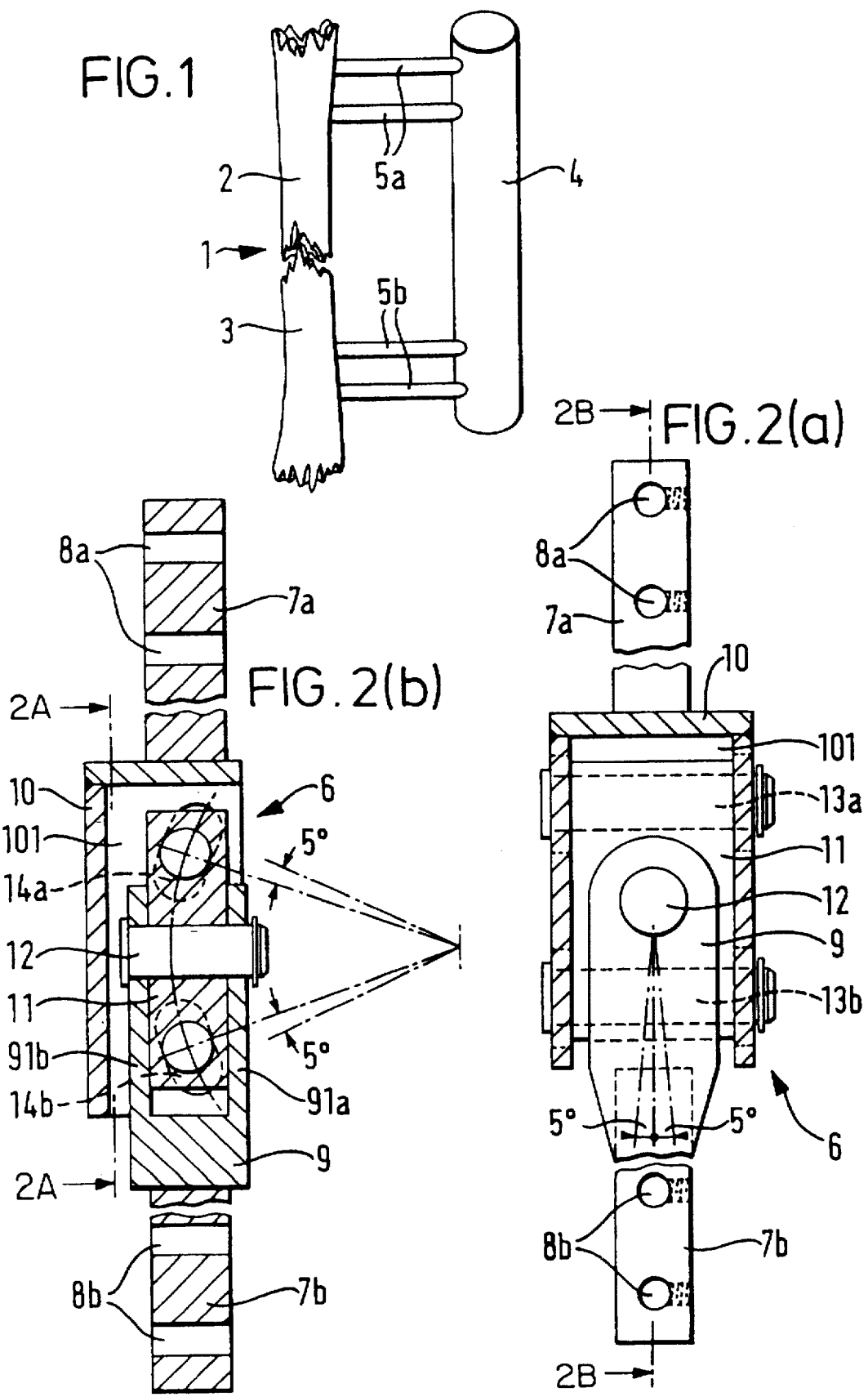

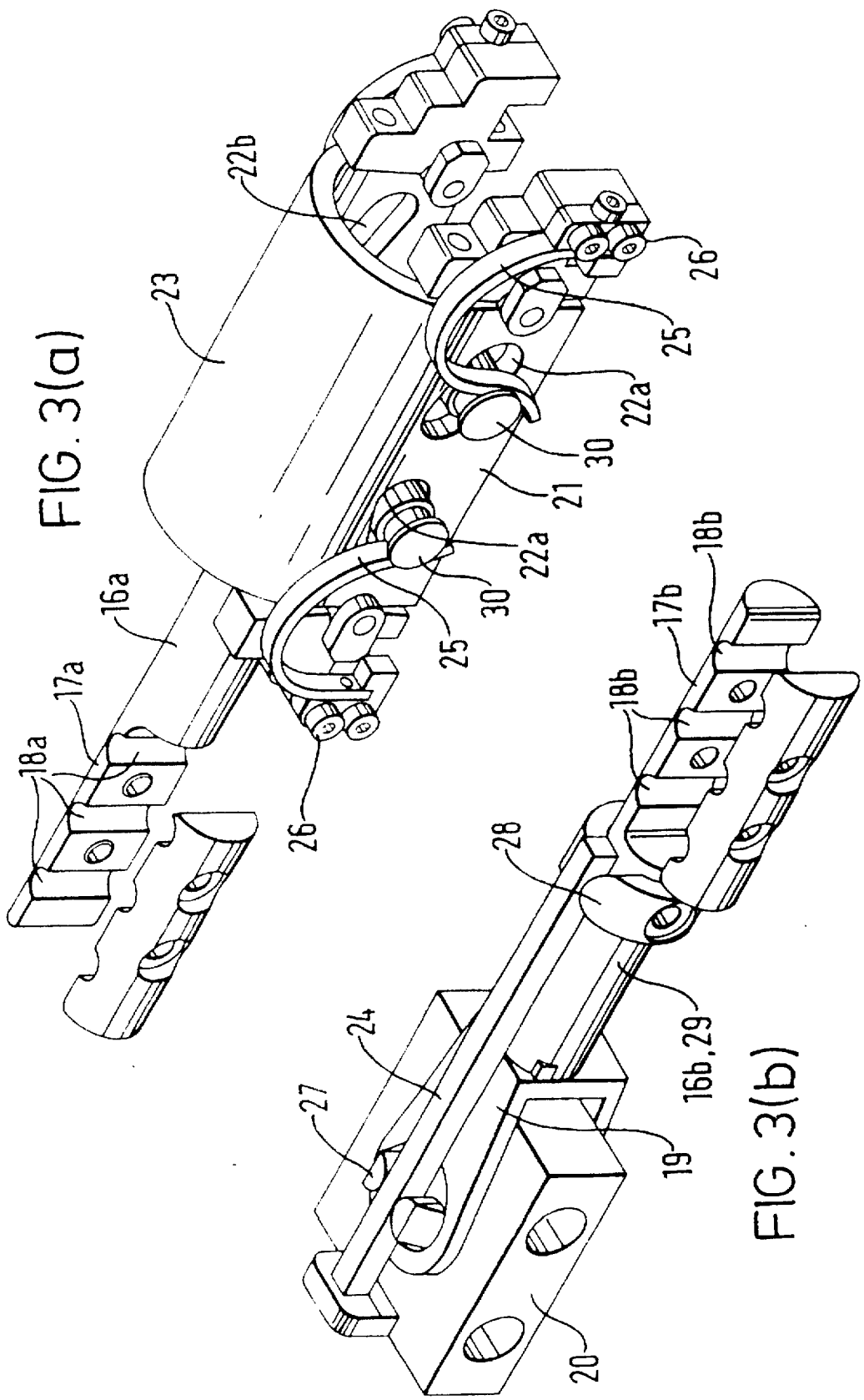

FIG.5(a)
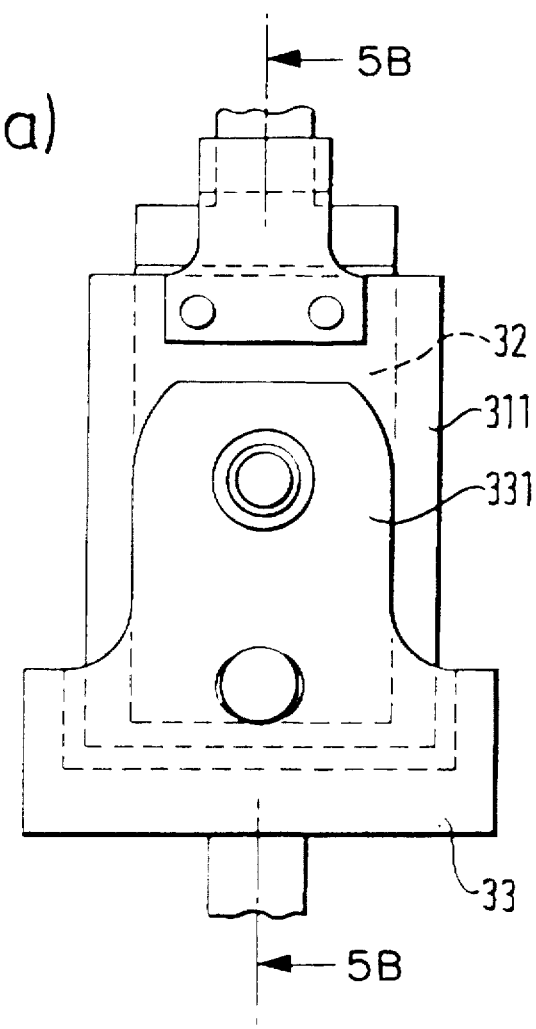
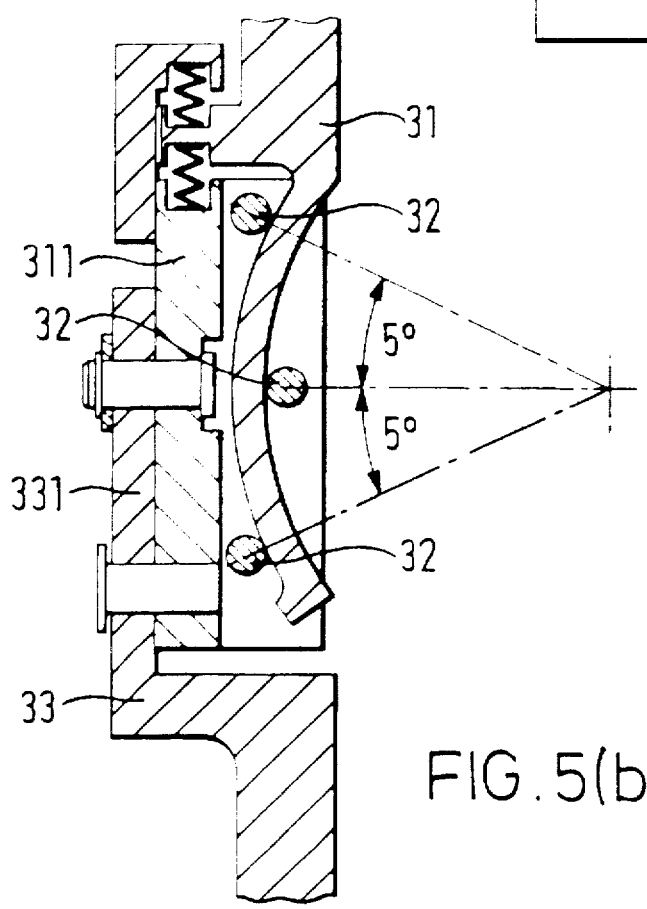
FIG.5(b)

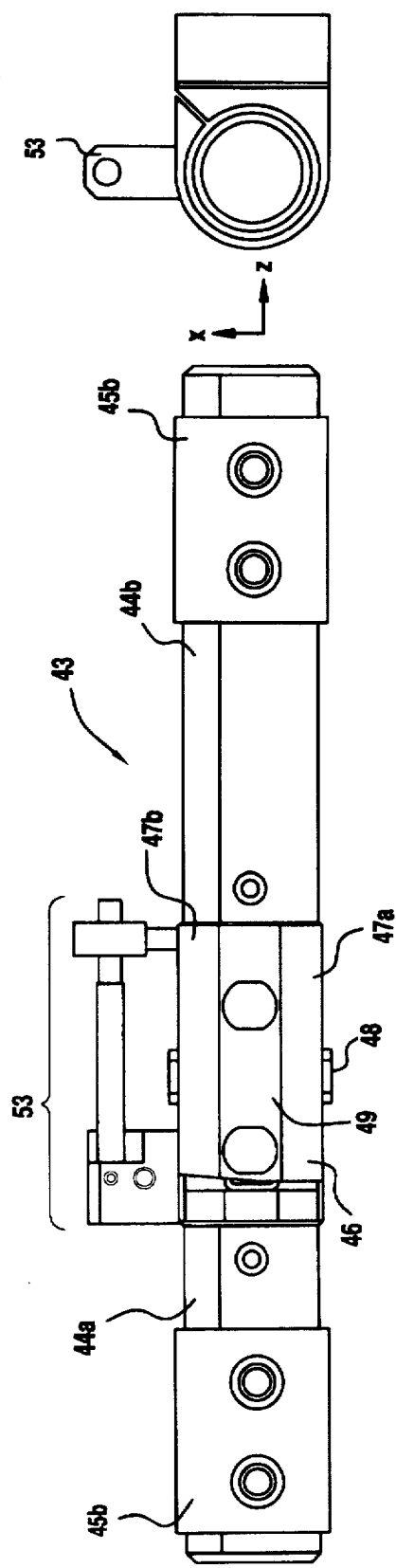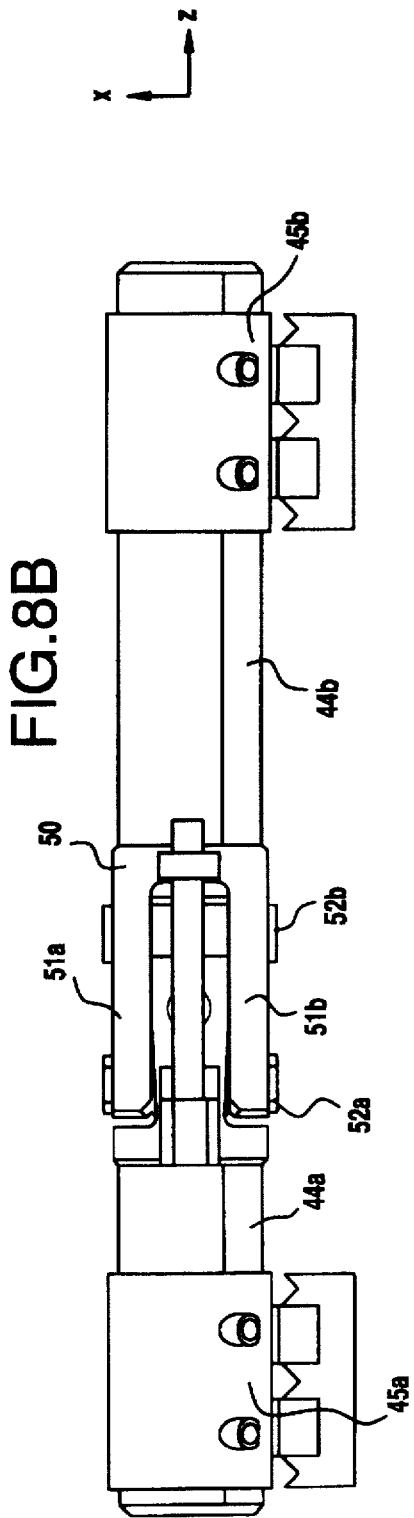

EXTERNAL BONE FIXATOR

FIELD OF THE INVENTION

This invention relates to a bone fixator. In particular it relates to an external bone fixator for use in the treatment of fractured bones such as the tibia and a method of monitoring the use of such a bone fixator.

BACKGROUND OF THE INVENTION

Bone is adept at self-healing, with new bone (callus) formation at the fracture site being able to reunite the fragments of the fractured bone. Medical treatment of fractured bone aims to assist and promote this natural healing.

One method of treatment involves the use of internal fixation whereby an implant (e.g. a bone plate) is directly attached to the bone fragments to rigidly hold them in place whilst healing takes place. Such treatment results in excellent alignment of the bone fragments. Such treatment does not allow relative motion between the two rigidly held bone fragments. Biological research has shown that certain types of callus formation is only triggered and maintained by relative motion of the bone fragments. Rigid fixation of the bone fragments therefore leads to a reduction in the formation of certain types of callus and therefore delays natural healing. Other types of medical treatment such as external supports (e.g. plaster of Paris casts), although allowing relative movement of the bone fragments and thereby promoting good callus formation, are not able to assist in precise and accurate bone fragment realignment. Attempts have therefore been made to develop devices for the treatment of bone fractures which hold the fragments sufficiently rigidly together to allow accurate realignment and yet at the same time allow sufficient relative movement between the bone fragments to promote and not inhibit callus formation.

DESCRIPTION OF PRIOR ART

One such attempt is the Orthofix external fixator, e.g. as described in EP-A-0011258. This device is applied externally to the injured limb and is attached to the bone fragments by bone pins or screws passing through the soft tissue of the limb into the bone. Bridging the gap between the pins in the two separate fragments is a rigid support bar, which holds the fragments in alignment. When the support bar is formed by telescopic elements the distance between the pin or set of pins attached to one of the bone fragments to the pin or set of pins attached to the other bone fragment can be varied. Such distance variation allows in theory for forced axial movement of the bone fragments relative to each other. This device suffers from the disadvantage that it is doubtful whether true axial movement occurs when it is applied to a tibia fracture. Once the fixator is unlocked axially, the fractured ends compress. There is then no force which would tend to pull the fractured ends apart again during normal movement. For this to occur, a strong spring would have to be introduced to hold the fractured ends apart so that they could be driven together by weight bearing. The fracture would then, however, be distracted, i.e. forced open, in the resting phase. Pneumatic, electromagnetic or electrical systems to overcome these problems would be expensive and cumbersome. It has also been found that relative axial motion promotes a long thin callus configuration which does not help to prevent the most common type of refracture.

In EP-A-0458486 a device is described which attempts to act as an external fixator which allows hinged movement about two separate planes. Although it is not clear how this device would work in practice, it is disclosed as being constrained to move in one hinged plane at a time. The constrained movement of the fixator could allow the bone fragments to move about a hinge in two planes only with respect to each other. This would lead to an uneven callus formation only along the lines of the hinged planes. To even out callus formation with this device it would be necessary for the position of the device relative to the bone fragments to be adjusted on a regular basis which would require repetitive visits to a medical practitioner.

Whilst many bone fixation systems, such as those discussed above, have been developed and some are presently in use clinically, there has been to date no means of accurately obtaining continuous information about their use in practice by patients. Obtaining such information would be of use in the assessment of the usefulness of current designs of bone fixation systems, in the development of future improved designs, and in the assessment of the efficient treatment of fractured bones.

SUMMARY OF THE INVENTION

There is therefore a need for an external fixator which allows for accurate realignment of bone fragments and at the same time allows movement around the fracture site to generate an even peripheral callus and this is an object of the present invention. Such allowed movement must be closely controlled to provide the desired type of relative movement only.

There is therefore a need for means by which the use of a bone fixation system can be monitored, and more particularly by which the use of an external bone fixator, which allows relative movement between fractured bones, can be monitored.

According to a first aspect of the present invention there is provided an external fixator for use in the treatment of a fractured bone having a first bone fragment and a second bone fragment which external fixator comprises:

means of attachment to the first bone fragment of the fractured bone;

means of attachment to the second bone fragment of the fractured bone;

a first rigid support bar having a first end and a second end, being connected to the first means of attachment at its first end and extending longitudinally therefrom;

a second rigid support bar having a first end and a second end, being connected to the second means of attachment by its first end and extending longitudinally therefrom;

a first movable element attached to the second end of the first support bar;

a second movable element attached to the second end of the second support bar, wherein the first movable element is movably mounted in the fixator so as to be capable of angular motion in one plane, and the second movable element is movably mounted in the fixator so as to be capable of angular motion in another plane, with the plane in which the second element moves being substantially orthogonal to the plane in which the first element moves, and the first and second movable elements are coupled together in such a way as to allow simultaneous angular movement of the external fixator in the two substantially orthogonal planes.

The first and second elements should be mounted so that the only relative motion allowed is the angular motion in the two substantially orthogonal planes, i.e. each of the first and second elements is only capable of movement in one orthogonal plane. It is not capable of any other type of movement.

When a fixator according to the present invention is attached to the bone fragments of a fractured bone, the fragments are held in alignment and the movement allowed corresponds to that possible in the fixator. (Some additional movement may be allowed via the bone pins or screws. This can be minimised by taking suitable measures such as shortening and thickening the pins or screws used.) The relative motion of the movable elements of the support bar is translated into controlled angular motion of the bone fragments around the bone fracture site. The fixator allows angular motion in any plane in which the longitudinal axis of the fracture bone lies. The loci of the allowed movement of one fragment to the other will be defined by shapes approximating to a cone. Other relative motions such as shear (translation), torsion (rotation) and axial motion are prevented by the fixator. The bone fragments can freely move angularly with respect to each other, i.e. they are free to hinge or pivot (flexion/extension) with respect to each other in any direction.

The controlled angular movement allowed by the fixator should be centred at the fracture site. The fixator should be positioned with respect to the bone fragments so that the substantially orthogonal planes are centred at the centre of the fracture site. To do this the axis about which the angular motion occurs of at least one of the coupled elements should lie substantially parallel to the longitudinal axis of the bone to be treated.

In order to obtain accurate remote centring of the fixator i.e. to obtain this parallel alignment, it is desirable to build into the fixator means of varying its alignment to the fractured bone. Where accurate bone pin alignment to the fracture site is possible, by which the fixator can be accurately aligned to the fractured bone, then it is not necessary to build into the fixator means of varying its alignment to the fracture. Such accurate pin alignment may be carried out by fixing the fractured parts together in their reduced state before drilling in the pins which are to hold the fixator. One particular method of accurately aligning the pins is as follows. Small diameter pins which are not required to pass right through the bone but need only penetrate the first cortex as they are not intended to be load bearing are applied to each of the bone fragments. Next a reduction device is used to accurately align the fractures, i.e. to accurately reduce them. Once the fracture has been satisfactorily reduced the fixation device of the present application is attached with two sets (e.g. of three pins each) of standard size weight bearing pins. As the bone fragments are held in place by the reduction device the pins can be precisely located with an alignment jig drill guide so that they are all parallel and in line and also perpendicular to the bone surface or longitudinal axis of the bone and so allow accurate orientation of the fixator.

The degree of relative angular movement allowed to the fractured bone fragments is dictated by the degree of angular freedom allowed in the fixation device. The upper limit of the permitted degree of movement is determined by the pain or a sense of instability which would be caused to or sensed by the patient by the corresponding movement of the fragments. If too large a degree of movement occurs unacceptable levels of pain will be experienced. A degree of angular freedom of plus or minus 5° for each of the first and second elements measured from their central resting position is presently considered suitable for the upper limit. A preferred upper limit for the permitted range of movement is in the order of plus or minus 2 to 3 plus or minus 2.5°.

The coupling of the first and second members may take any suitable form.

The fixation device may be provided with a third or coupling member to which the first and the second members are each mounted, i.e. the first and second members may be coupled together by a third or coupling member. In such a case either the first or second or both members may be pivotally mounted on the third or coupling member.

Pivotal mounting of the movable elements may be accomplished by mounting on a pivot pin. Alternative pivotal mounting can be achieved by provision of an arc-shaped cam surface on which a suitably provided follower can be guided. The movable member can be provided with an arc-shaped cam surface, e.g. an arc-shaped slot or passage or housing, or with a cam follower which follows a cam surface provided on another component of the fixator, e.g. on the third or coupling member.

In a preferred embodiment the first member is pivotally mounted on a third member by means of a pivot pin about which it is able to pivot and the second member is provided with one or more projections which are received within one or more arc-shaped slot on the third member.

For a compact design one of the first or second movable members may take the form of an open housing into which the other member may be received. If present the third or coupling member may also be received within the housing. The dimensions of the housing may be used to limit the degree of freedom of movement of the movable member mounted within it. Alternatively the first and second members may each take the form of a two-limbed member in the substantial form of the head of a tuning fork. The two members are then positioned orthogonally to each other and joined by the third or coupling member.

At their non-coupled ends the first and second member may be suitably shaped so as to function as support rods. The support rods may instead of being integral, however, be separate from (but connected to) the coupled movable elements. In this latter case the support rods and movable elements together form the support bar.

It is desirable for the fixator to incorporate return mechanisms to return one or both of the movable elements of the fixator to its central position when unloaded. This will allow accurate alignment of the fracture when the limb is at rest. The return mechanism could take the form of a spring, i.e. a component which deflects under stress and returns to its original dimensions and configurations when the stress is removed. A return mechanism may be associated with each of the movable elements. The return mechanism associated with the first element may differ from or be the same as that associated with the second element.

The means of attachment of the support bar to the bone fragments may take any suitable form. It is usual for external fixation devices to be fixed to the bone fragments by percutaneous or transcutaneous pins or screws, i.e. pins or screws which transect the skin. Such bone pins or screws may either be transfixion pins, i.e. ones which pass completely through the bone and limb and emerge on the other side, or half pins which fasten into the bone and do not emerge therefrom. If transfixion pins are used a fixator can be attached on either end of the pins, i.e. a fixator can be attached on either side of the limb (bilateral). If half pins are used only one fixator will be attached on only one side of the limb (unilateral).

The fixation device may be attached to the bone fragments by any suitable number of pins, e.g. one, two or more. It is preferred that three pins are used to attach to each bone fragment as this number leads to good stress reduction at the bone interface and would allow for the removal of one pin if necessary, leaving two for sufficient stability. If only two pins were used and one was required to be removed, further operation may be required for the insertion of another pin to ensure stability. Each of the pins should be in substantially parallel alignment with its neighbors.

The fixator then requires means of attachment, for example clamps, able to fixedly attach to the bone pins or screws. Such means may be integral with or separate from the support bar, e.g. the coupled movable elements or the support rods. The attachment means, e.g. clamps, can have any suitable design but should be adapted to allow for easy attachment of the fixator to the bone pins or screws irrespective of their relative positioning and alignment. For this purpose the clamps may, for example, be provided with means to adjust their orientation within a reasonable range of diversion to allow connection to the bone pins attached to each of the bone fragments. Preferably the clamps are provided with the possibility of movement in three planes, i.e. so that they have 6 degrees of freedom of movement. Movement in each of these planes must be lockable so that final alignment can be maintained. Such adaptation could include the use of ball joints.

In use to reduce the mechanical stresses induced on the fixator/pin connection and throughout the rest of the fixation device, it is preferably for each means of attachment, e.g. clamp, to be positioned as close to the skin of the limb being treated as possible to minimise the effect of bending moment. However, since direct contact between the external structure and the soft tissue is medically inadvisable a minimum clearance of at least 1 cm is recommended.

The fixator is preferably provided with a disabling mechanism by which the controlled angular motion may be prevented. By this mechanism the fixator would be converted to a rigid external fixator.

The fixator device of the present application is particularly suitable for the treatment of fractures which have occurred to the tibia.

The fixator may be made of any suitable material, such as those used conventionally in orthopaedic and prosthetic components. Such materials are those which are corrosion resistant, cleanable and sterilisable. The material is preferably X-ray transparent or translucent to allow X-rays of the fracture to be carried out whilst the fixator is in place. Carbon fibre composites are suitable materials that would be X-ray translucent.

The material chosen for the device may be such as to reduce its weight to a minimum, e.g. cast aluminium high strength alloys could be used.

The present invention is advantageous as it will allow improved fracture healing which will benefit the patient and also reduce demands on the Health Service. Furthermore, the present fixator is easy to accurately apply and requires little or no readjustment during the healing process. Conventional fixation devices in contrast may require second or third time adjustment of the fixator, some times under anaesthetic, either due to incorrect original alignment or to vary the range of permitted motion of the fragments at the fracture site. With the present invention subsequent adjustments are reduced to a minimum and the device itself cannot go out of alignment. This will reduce the stress to the patient of extra operations and will also relieve valuable operating time. The patient will benefit from reduced healing time and improved mobility. Patients may be able to return to work in a shorter period. Further the controlled angular motion within the fracture site provided with the present invention leads to an approximately spherical or fusiform mass of callus which is best able to resist the commonest mode of refracture. With the fixator of the present invention such callus formation is easily activated by the movement of ambulation. The fixator also prevents the harmful movements of shear and rotation and prevents shortening in a fracture which is axially unstable.

According to a second aspect of the present invention there is provided a bone fixation system for use in the treatment of a fractured bone, which fixation system is provided with a data logging device which is capable of sensing and storing data relating to the frequency of occurrence of an event associated with at least one physical characteristic of the fixation system.

According to the present invention there is also provided a method of monitoring the use in the treatment of a fractured bone of a bone fixation system, which method comprises sensing and storing data relating to the frequency of occurrence of an event associated with at one least one physical characteristic of the fixation system using a data logging device with which the fixation system is provided.

With the present invention it is possible to accurately obtain continuous information about the use of the fixator by the patient.

The data logging device may be separable from the fixation system or it may be an integral part thereof. It may, for example, be optionally removably attached to a suitable part of the fixation system. It may be so attached externally or more preferably internally, e.g. within a support bar or limb of the fixation system.

The data logging device must be capable of recording data in a form in which it can be readily used by a computer. In general terms in the data logging device information about the frequency of occurrence of the event associated with a physical characteristic which is being sensed is fed via a suitable transducer, which converts it into a usable signal, to a memory where it is recorded and stored. The data logging device may at a convenient point in time be suitably connected to a computer for downloading, i.e. reading of the data stored in the memory. The data logging device may be adapted so that it can be downloaded whilst the fixation system is still in use by a patient (i.e. whilst it is still in place on the limb of the patient), alternatively either the data logger alone or the fixation system incorporating the data logger can be removed from the patient and downloaded in isolation.

The data logging device must be portable so as not to hinder the free movement of the patient using the fixation system. It should, therefore, be independently powered, e.g. using suitable batteries.

If it is desired to sense or record the number of times a specific event relating to a physical characteristic takes place within a certain time interval the data logging device could be provided with a clock of suitable form.

The data logging device can be adapted to sense the occurrence of any desired characteristic or characteristics. Examples of physical characteristics which may be sensed are relative position, strain, pressure, and displacement. Information regarding displacement of the fixation system or components of the fixation system is particularly useful as it can be analysed to directly relate to bone callus formation and fracture healing. Various aspects of displacement of the fixation system and its components may be monitored using the present invention, e.g. the type of displacement (axial, lateral/medial, posterior/anterior, angular etc.) and the degree or extent of displacement. The data logger is programmed to log the occurrence of an event when it senses a certain predetermined limit of the physical characteristic being sensed. If relative movement in a given plane is being sensed the data logger may record that an event has taken place when a certain amount of movement in that plane has been sensed. Movements below the predetermined limit will be ignored. The data logger may need to be individually calibrated for each patient. The present invention could, for example, be used to record the number of times a given (predetermined) level of displacement occurred in two individually sensed orthogonal planes in a given time interval, e.g. a half hour. Such recording could take place continuously throughout the day and could provide information as to how regularly the fixation system or one or more of its components was displaced. Where displacement in the fixation system is directly related to displacement of the fractured bones such information could be used to investigate the amount or type of relative movement occurring at the fracture site. Little displacement would be expected initially whilst the affected limb was too painful to move. Displacement should increase as the patient began to use the limb more but the fractured bones were still relatively mobile. Displacement frequency should decrease again with time as callus formation increased and "knitted" the bones back together preventing relative movement. Information on displacement frequency could therefore show how healing was progressing. This will aid the physician in charge of the patient in determining whether initiation of the healing processes has taken place and when complete healing can be expected. The logged information could also show that an observed patient was not moving enough to promote healing. The invention could therefore also be used as an aid to motivate patients to take an active role in the healing process.

The data logging device or the fixation system could be provided with indicator means which indicated when a certain individual event or condition, as measured by the data logger, had occurred. It could also show whether given levels of frequency of event, e.g. displacement, had occurred. This could motivate patients to move more if certain target frequencies of displacement were not reached as shown by the indicator.

The present invention may be used with any suitable bone fixation system and preferably one that allows relative movement of the bone fragments. It could for example be used with an internal fixation system but more preferably it is used with an external bone fixation system. Suitable external fixation systems include external supports, such as a plaster of paris cast or curable resin support or any type of external bone fixator. It may, for example, be used with an external bone fixator which allows relative movement between the bone fragments. One such fixator is the Orthofix™ external fixator, e.g. as described in EP-A-0011258. In such a fixator the support bar or mechanism is formed by telescopic elements, so that the distance between the pin or set of pins attached to one of the bone fragments to the pin or set of pins attached to the other bone fragment can be varied. Such distance variation allows for forced axial movement of the bone fragments relative to each other.

Another fixator which is particularly preferred for use in the present invention allows relative angular movement of the fractured bones, e.g. as described above in relation to the first aspect of the present invention.

The means of attachment of the fixation system to or around the bone fragments may take any suitable form such as that used conventionally for the type of fixation system in question. It is usual for external fixators to be fixed to the bone fragments by percutaneous or transcutaneous pins or screws, i.e. pins or screws which transect the skin. Such bone pins or screws may either be transfixion pins, i.e. ones which pass completely through the bone and limb and emerge on the other side, or half pins which fasten into the bone and do not emerge therefrom. If transfixion pins are used a fixator can be attached on either end of the pins, i.e. a fixator can be attached on either side of the limb (bilateral). If half pins are used only one fixator will be attached on only one side of the limb (unilateral). The fixator may be attached to the bone fragments by any suitable number of pins, e.g. one, two or more. It is preferred that three pins are used to attach to each bone fragment as this number leads to good stress reduction at the bone interface and would allow for the removal of one pin if necessary, leaving two for sufficient stability. If only two pins were used and one was required to be removed, further operation may be required for the insertion of another pin to ensure stability. The fixator should have means of attachment, for example clamps, able to fixedly attach to the bone pins or screws. Such means may be integral with or separate from the fixator itself.

The fixation system and its data logging device may be made of any suitable material, such as those used conventionally in orthopaedic and prosthetic components. Such materials are those which are corrosion resistant, cleanable and sterilisable. The material is preferably and where possible X-ray transparent or translucent to allow X-rays of the fracture to be carried out whilst the fixation system is in place. Carbon fibre composites are suitable materials that would be X-ray translucent.

The material chosen for the data logging device may be such as to reduce its weight to a minimum, e.g. cast aluminium high strength alloys could be used.

The present invention is advantageous as it will allow the use of bone fixation systems, including those which allow relative movement of fractured bones, to be monitored and assessed. This will provide information useful in the assessment of current designs of fixation systems, in the development of future improved designs and in the assessment of the efficient treatment of fractured bones, e.g. to predict optimum fracture healing time. The invention will allow monitoring of the fracture over a period of weeks even months.

BRIEF DESCRIPTION OF THE DRAWINGS

For a better understanding of the present invention and to show how the same may be put into effect reference will now be made, by way of example, to the accompanying drawings, in which:

FIG. 1 is a schematic view of an external fixator attached to a fractured bone;

FIGS. 2 a) and b) are cross-sectional views of a first embodiment of the present invention;

FIGS. 3 a) and b) are perspective views of the individual components of a second embodiment;

FIGS. 5 a) and b) are front elevational and cross-section views of a third embodiment of the present invention;

FIGS. 8 a), b) and c) are front, side and end elevational views of a sixth embodiment.

DETAILED DESCRIPTION OF THE INVENTION

Figure 4:
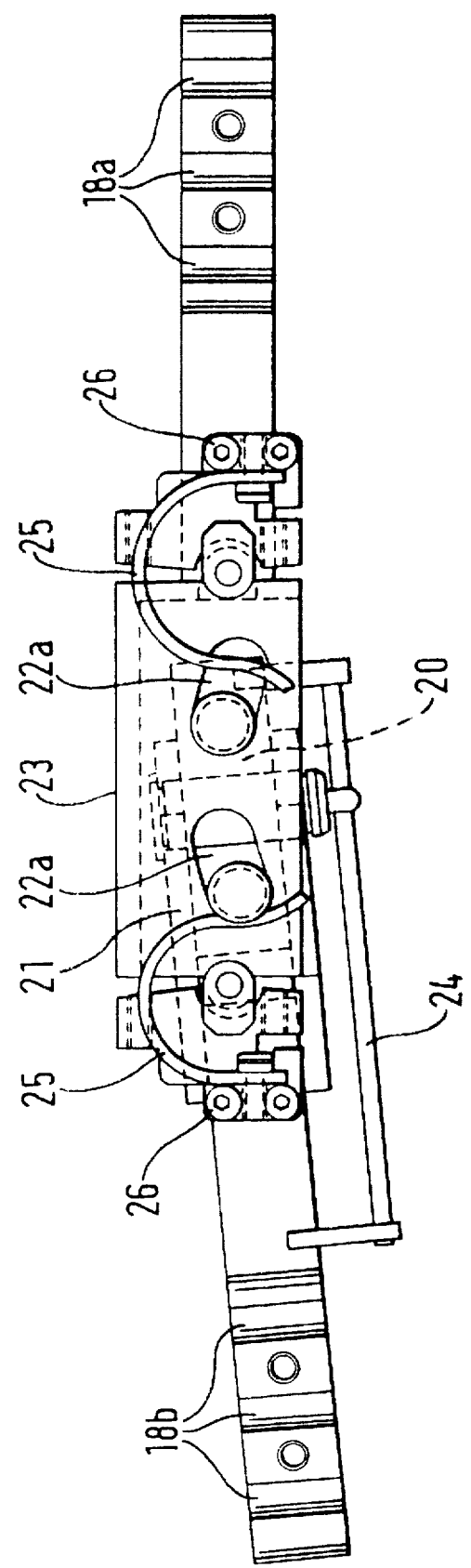
FIG. 4 is a side view of the assembled components of the second embodiment shown in FIG. 3.

In FIG. 1 a fractured bone 1 is shown, which has been broken into an upper fragment 2 and a lower fragment 3. Support is given to the fractured bone by an external fixator 4. The fixator 4 is in the form of rigid support bar extending substantially parallel to the longitudinal axis of the bone (or as close to parallel thereto as is possible). It is attached to the upper and lower fragments 2 and 3 by two pairs of bone pins 5a, 5b which extend in parallel to each other and substantially perpendicularly to the longitudinal axis of the bone 1.

In FIG. 2 a first embodiment of a fixator according to the present invention is shown. The fixator 6 of the embodiment has two rigid support arms or rods 7a, 7b which extend along the longitudinal axis of the fixator 6, which in use should be substantially parallel to the longitudinal axis of the bone. Towards their extremities the support rods 7a, 7b are each provided with two channels 8a, 8b perpendicularly extending right through the support rods 7a, 7b. These channels 8a, 8b are used for receiving bone pins or screws, which may be clamped therein (e.g. by screws) to fixedly attach the fixator 6 to a fractured bone in which the pins are implanted. The support rods 7a, 7b are each attached at their other ends to one of the movable elements of the fixator. The first movable element 9 is U-shaped in side elevation and is formed from two substantially parallel extending limbs 91a, 91b rising up from a support base 92. Towards their distal ends the limbs 91a, 91b are each provided with an aperture. The second movable element 10 takes the form of an open-ended chamber or housing 101. In this embodiment it is substantially cuboid having one end wall and two side walls but no top or other end wall. The first movable element 9 is mounted within the second movable element 10 and extends out of the open end wall. The two elements 9, 10 are coupled together by a block 11 which is accommodated within the chamber of the second movable element 10 and acts as a third or coupling element. The movable elements 9, 10 are both movably attached to the block 11, which in this embodiment is cuboid. The block 11 fits within the limbs 91a, 91b of the first movable element 9. The first movable element 9 is pivotally mounted on the block 11 by a pivot pin 12 which extends perpendicularly to the longitudinal axis of the fixator 6 (and in use also of the bone). The first element 9 is able to pivot about pin 12 by about two and a half degrees in either direction. It is constrained from larger degrees of angular movement by the dimensions of the chamber 101 of the second element 10. The second element 10 is mounted on the block 11 by two pins 13a, 13b which extend through the block 11 substantially orthogonal to the pivot pin 12 by which the first element 9 is mounted. These substantially orthogonal pins 13a, 13b are mounted in pairs of radial slots 14a, 14b a pair of which are provided on each side wall of the second element 10. Relative to the first element 9 and the block 11, the second element 10 is able to move about the fixing pins 13a, 13b along an arced path defined by the radial slots.

In use the pivot pin 12 should be aligned with the level of the fracture and the fixator 6 clamped on to pins fixed in the bone at a distance from the bone so that the centre of the arc along which the second element 10 moves is substantially at the centre of the fracture site.

In this manner the centre of rotation of the fracture site is projected using a remote centre arrangement. In this way the fixator 6 is caused to respond to a given movement in the same way that it would do if it had been directly acted upon by the same movement at the fracture centre.

The second embodiment, i.e. that shown in FIGS. 3 and 4, is very similar to the first embodiment but includes a return mechanism to return the fixator back to its central position when unloaded to ensure that the fracture is aligned correctly when the limb is at rest. The fixator 15 of the second embodiment also has an upper support rod 16 and a lower support rod 29, each of which is provided with means of attachment to bone pins. In this case those means are individual parts of clamps 17a, 17b provided with channels 18a, 18b through which the bone pins can extend and which can be held together by screws (not shown).

The first movable element 19 is pivotally mounted in a central block 20 as in the first embodiment. The second element 21 is movably mounted via radial slots 22a, 22b as in the first embodiment. It is protected in this case by a domed protective covering 23. The return mechanisms take the form of springs acting in both axes of angular motion. The first movable element 19 is acted upon by a single cantilever spring 24 and four flat semi-circular springs 25a, 25b act upon the second movable element 21. The semi-circular springs 25a, 25b are held by four independently adjustable spring holders 26a, 26b that are adjustable to meet the needs of the individual patient.

The cantilever spring 24 which acts as the return mechanism for the first element 19 is seen in FIG. 3b running along the top from the left towards the pin grip assembly (the clamps 17a, 17b). The pivot point of the cantilever spring 24 is through the centre of the pivot pin 27 of the first element 19 and the load is applied by a radial clamp 28 which is fixed to the support rod 29 by screws (not shown). To adjust the stiffness of the cantilever spring 24 the radial clamp 28 is able to slide up and down the lower support rod 29. The pivotal pin 27 holding the first movable element 19 in place is in turn held in place by the axis pins 30a, 30b by which the second movable element 21 is mounted as they pass through the central block 20.

To lock the device, immediately after the fracture has occurred or subsequently in the case of a problem or to be able to study the effects of motion in a clinical trial, two screws could be inserted in the top of the second element 21 at both ends to lock the first plane of movement and to lock the second plane another screw could be inserted into the central block 21 by the lower rod 29.

In the embodiment shown in FIG. 5 the second movable element 31 does not take the form of a housing but an arced plate, running between three pins 32 provided in a central block 311. The first movable element 33 is again in the form of the simple pivot, this time only having one limb 331 extending from a support base. The arced plate 31 is located within the confines of the pivotal movement of the first element 33 so that in use they operate at the same level as the fracture when properly aligned.

Figure 6:
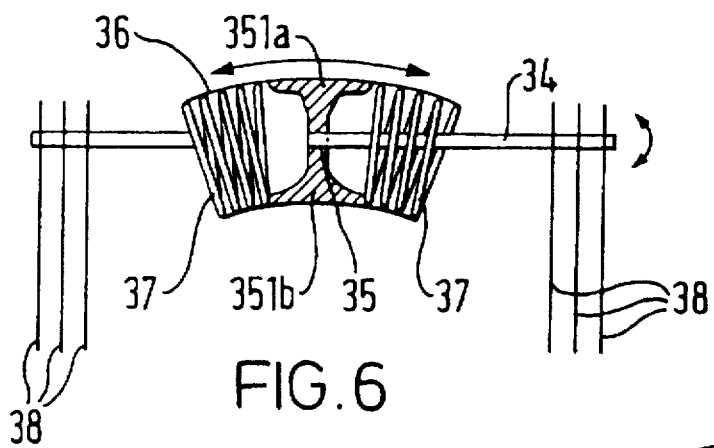
FIG. 6 is a schematic view of a fourth embodiment.

In the embodiment of FIG. 6, the first element 34 is an elongate bar which is mounted again by a simple pivot pin. The third or coupling element 35, to which the first element is directly pivotally mounted, takes the form of a block having at either side a perpendicularly extending arm 351a, 351b, one of which is concave and the other convex. The third or coupling element 35 is slidingly mounted within the second element which takes the form of a guide housing 36. The guide housing 36 is shaped to provide an arced guide path for itself over the third element 35. A return mechanism for the second element 35 takes the form of compression springs 37 mounted within the guide housing 36 which are acted upon by the block of the third document. This embodiment is shown attached to bone pins 38a, 38b.

Figure 7A:
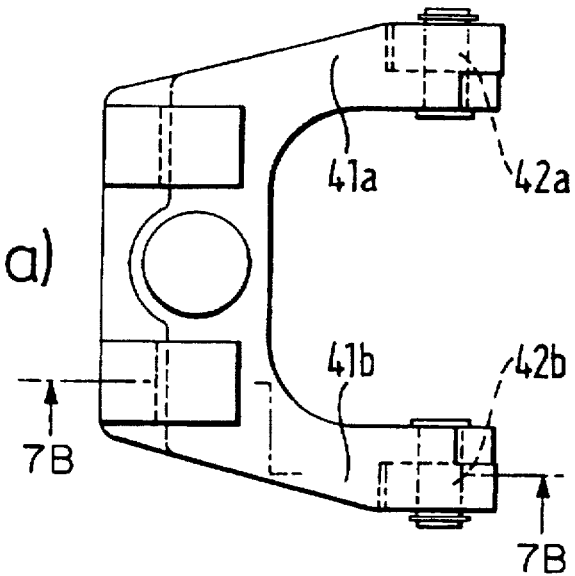
FIGS. 7 a), b) and c) are planar, cross-sectional and side elevational views of a fifth embodiment.
Figure 7B:
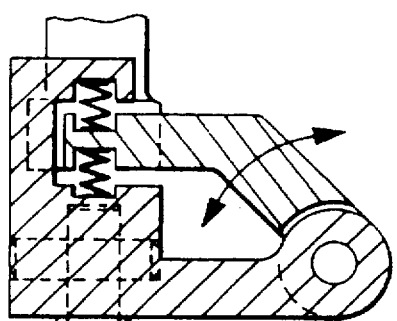
Figure 7C:
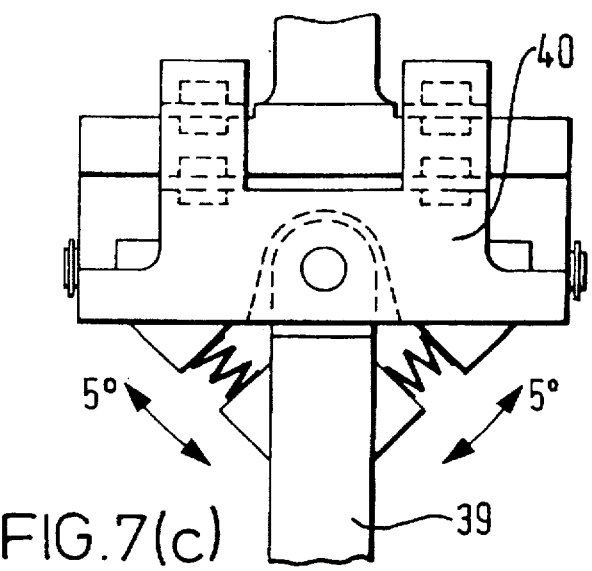

In the embodiment of FIG. 7 the first element 39 is an elongate rod mounted again by a simple pivot pin. The second element 40 is also pivotally mounted. To pivot in a plane substantially orthogonal to that of the first element 39, the second element 40 has two arms 41a, 41b which extend perpendicularly to the longitudinally axis of the fixator (which in use which also be perpendicularly to the longitudinal axis of the bone) and is pivoted about two pins 42a, 42b which extend orthogonal to both the fixator's longitudinal axis and the arms 41a, 41b. In use the limb to be treated would be received within the two arms 41a, 41b of the second member 40 and the pivot pins 42a, 42b would be lined up with the fracture site.

The embodiment shown in FIG. 8 is similar to those described above in relation to FIGS. 2, 3 and 4 save that both the first and second movable members take the form of a two parallel limbed member which forked members are orthogonally interlocked. More particularly the fixator 43 shown in FIG. 8 has two longitudinally extending rigid support arms or tubes 44a, b each having at their ends a pin clamp assembly 45a, b for receiving bone pins (not shown) fixed to the fractured bones. At the other ends the rigid support tubes 44a, b are attached to the movable elements. The first movable element 46 is substantially in the form of a tuning fork and is generally U-shaped in side elevation being formed by two substantially parallel extending limbs 47a, b. The first movable element 45 is pivotally mounted by means of a pivot pin 48 on a central block 49 which fits within the parallel extending limbs 47a, b and acts as the third or coupling element. The second movable element 50 also takes the substantial form of a tuning fork and has two substantially parallel limbs 57a, b which are positioned orthogonally to those of the first movable element 45. The second movable element 50 is mounted on the central block for pivotal motion in a plane orthogonal to the pivotal motion of the first movable element 45 by means of two pins 52a, b which are movable along an arc defined by radial slots in the central block 49. Controlled angular motion is achieved through the central joint of the fixator 43 allowing movement in two orthogonal planes. In the direction passing through the fracture, termed the x axis, the simple pivot 48 allows angulation, for which the first movable element 45 pivots about the central block 49. In the orthogonal axis, termed the y axis, the fixator is displaced with respect to the fracture by the two pins 52a, b which slide within the arcs centred on the fracture site provided in the central block 49. Resistance to the applied movements is achieved via a cantilever spring system 53. Angulation about the x axis cause the cantilever spring to be displaced by a distance Ay and therefore provides an opposing force to that angulation. Angulation about the y axis cause the cantilever spring to be displaced by a distance Ax which provides an opposing force to that angulation.

In use the affected limb, e.g. a leg, is prepared under general anaesthetic. A pair of percutaneous fixation screws are inserted into both tibial fracture fragments. The fracture is then reduced (i.e. the fragments are brought together and realigned) using a separate reduction device. Further percutaneous screws are then inserted, e.g. three above and three below the fracture, to enable correct centring of the substantially orthogonal movement planes of the fixation device at the centre of the fracture. The fixation device is then applied to these fixed screws, its exact position being verified by reference to the previous screws used for reduction or by X-rays. The reduction device and the associated screws are then removed and the wounds made by them closed.

The fixation device according to the present invention is such that angular motion can be induced so that the fracture fragments can be flexed with respect to each other while still maintaining their relative orientation at the fracture site at rest. At the same time they are constrained from relative translation and therefore shearing.

Figure 9:
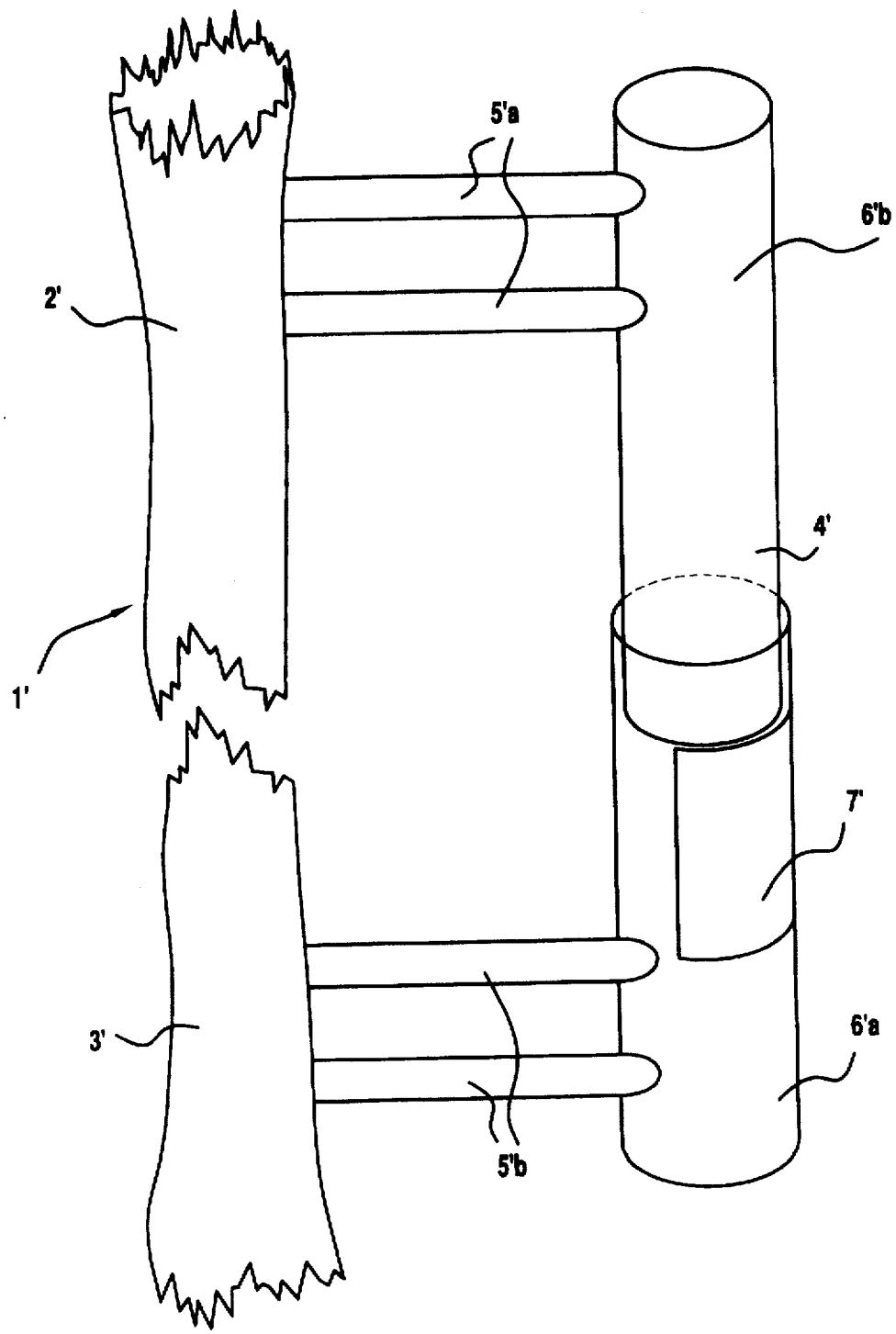
FIG. 9 is a schematic view of another external fixator attached to a fractured bone.

In FIG. 9, which is schematic only, a fractured bone 1' is shown, which has been broken into an upper fragment 2' and a lower fragment 3'. Support is given to the fractured bone by an external fixator 4'. The fixator 4' is in the form of rigid support bar extending substantially parallel to the longitudinal axis of the bone (or as close to parallel thereto as is possible). It is attached to the upper and lower fragments 2' and 3' by two pairs of bone pins 5'a, 5'b which extend in parallel to each other and substantially perpendicularly to the longitudinal axis of the bone 1'.

In this embodiment the support bar 4' is divided into a first (lower) component 6'a and a second (upper) component 6'b, which fits and slides within the first component 6'a. The telescoping of the two components 6'a, 6'b, i.e. their relative axial movement, leads to corresponding relative axial movement between the bone fragments 2' and 3'.

The data logger 7' is accommodated (out of the patient's sight) within the support bar 4'. It is provided with means by which it senses the relative axial displacement of the components 6'a, 6'b of the support bar 4'. It is calibrated to record as the occurrence of an event the sensing of an amount of axial displacement over and above a pre-set minimum. It may be programmed to count the number of times that certain level of axial displacement occurs during a given period, e.g. 30 minutes. That information may then be relayed via a transducer to the memory of the data logger for recording and storing for subsequent reading.

It is to be understood that the above detailed description of preferred embodiments of the invention is provided by way of example only. Various details of design and construction may be modified without departing from the true spirit and scope of the invention, as set forth in the appended claims.

We claim:

1. An external fixator for use in the treatment of a fractured bone having a first bone fragment and a second bone fragment which external fixator comprises:

means of attachment to the first bone fragment of the fractured bone;

means of attachment to the second bone fragment of the fractured bone;

a first rigid support bar having a first end and a second end, being connected to the first means of attachment at its first end and extending longitudinally therefrom;

a second rigid support bar having a first end and a second end, being connected to the second means of attachment by its first end and extending longitudinally therefrom;

a first movable element attached to the second end of the first support bar;

a second movable element attached to the second end of the second support bar, a coupling member attached to the second ends of the first and second movable elements;

wherein the first movable element is movably mounted to the coupling member which limits the first movable element to acutely angular motion in one plane, and the second movable element is movably mounted to the coupling member so as to be limited to acutely angular motion in another plane, with the plane in which the second element moves being substantially orthogonal to the plane in which the first element moves, and the first and second movable elements are coupled together in such a way as to allow simultaneous limited angular movement of the external fixator in the two substantially orthogonal planes such that the first bone fragment is angularly displaceable with respect to the second bone fragment about the fracture site, such angular displacement being limited by the fixator.

2. A fixator according to claim 1, in which the angular motion of the first movable element is centered at a first center point and the angular motion of the second movable element is centered at a second center point and the first and second center points lie in a common plane and in use the external fixator is positioned with respect to the bone fragments so that the common plane passes through the centre of the fracture site.

3. A fixator according to claim 1, wherein the relative angular displacement of the first and second bone fragments is limited to less than 10°.

4. A fixator according to claim 3, wherein the relative angular displacement is limited to less than 4° to 6°.

5. A fixator according to claim 1, wherein the first member is pivotally mounted on the coupling member.

6. A fixator according to claim 1, wherein the second member is pivotally mounted on the coupling member.

7. A fixator according to claim 1, wherein the first movable element takes the form of an open housing in which the second movable element is at least partially accommodated.

8. A fixator according to claim 1, which further includes a coupling member to which the first and the second movable element is attached and the coupling member is received within at least one of the movable elements.

9. A fixator according to claim 1, wherein the first movable element is substantially in the shape of a tuning fork and has two parallel extending limbs and the second movable element is substantially in the shape of a tuning fork and has two parallel extending limbs and is positioned orthogonally with respect to the first movable member.

10. A fixator according to claim 9, which further includes a coupling member positioned between the limbs of the first and second movable members, the first and second movable members being pivotally mounted on the coupling member.

11. A fixator according to claim 1, which includes a return mechanism capable of returning one of the movable elements of the fixator to its central position when unloaded.

12. A fixator according to claim 1, wherein each movable element is provided with a return mechanism for returning it to its central position when unloaded.

13. A fixator according to claim 12, wherein the return mechanism takes the form of a spring.

14. A bone fixation system for use in the treatment of a fractured bone having a first bone fragment and a second bone fragment, comprising:
an external bone fixation system for attachment to a fractured bone during healing of the fractured bone;
a data logging device which is carried by the system and which operates constantly while the system is attached to the fractured bone so as to monitor the first and second bone fragments and the system, so as to sense and store data indicating the frequency of occurrence of an event associated with at least one characteristic of the fractured bone and the system.

15. A system according to claim 14, wherein the data logging device is adapted to sense one or more of the following characteristics: relative position, strain, pressure, and displacement.

16. A system or method according to claim 15, wherein the data logger is adapted to sense the type of displacement (axial, lateral/medial, posterior/anterior, angular etc.) or the degree or extent of displacement.

17. A system according to claim 14, wherein the data logging device or the fixation system is provided with indicator means which indicates when a certain event or condition or a certain frequency of events, as measured by the data logger, has occurred.

18. A system according to claim 14, wherein the external bone fixation system is an external support, such as a plaster of paris cast or curable resin support, or a type of external bone fixator.

19. A system according to claim 14 wherein the external bone fixation system allows controlled angular displacement of the bone fragments with respect to one another in the vicinity of the bone fracture site.

20. A system according to claim 19, wherein the external fixator comprises:
means of attachment to the first bone fragment of the fractured bone;
means of attachment to the second bone fragment of the fractured bone;
a first rigid support bar having a first end and a second end, being connected to the first means of attachment at its first end and extending longitudinally therefrom;
a second rigid support bar having a first end and a second end, being connected to the second means of attachment by its first end and extending longitudinally therefrom;
a first movable element attached to the second end of the first support bar;
a second movable element attached to the second end of the second support bar,
wherein the first movable element is movably mounted in the fixator so as to be capable of angular motion in one plane, and the second movable element is movably mounted in the fixator so as to be capable of angular motion in another plane, with the plane in which the second element moves being substantially orthogonal to the plane in which the first element moves, and the first and second movable elements are coupled together in such a way as to allow simultaneous angular movement of the external fixator in the two substantially orthogonal planes.

21. An external fixator for use in the treatment of a fractured bone having a first bone fragment and a second bone fragment which external fixator comprises:
means of attachment to the first bone fragment of the fractured bone;
means of attachment to the second bone fragment of the fractured bone;
a first rigid support bar having a first end and a second end, being connected to the first means of attachment at its first end and extending longitudinally therefrom;
a second rigid support bar having a first end and a second end, being connected to the second means of attachment by its first end and extending longitudinally therefrom;
a first movable member attached to the second end of the first support bar;
a second movable member attached to the second end of the second support bar; and a coupling member by which the first and second movable members are coupled together, the first and second members being pivotally mounted on the coupling member, by means of locating pins, wherein the first movable member is limited to acutely angular motion in one plane by the coupling member, and the second movable member is limited to acutely angular motion in another plane, with the plane in which the second element moves being substantially orthogonal to the plane in which the first element moves, and the first and second movable elements are coupled together in such a way as to allow simultaneous limited angular movement of the external fixator in the two substantially orthogonal planes such that the first bone fragment is angularly displaceable with respect to the second bone fragment about the fracture site, such angular displacement being limited by the fixator.

22. A fixator according to claim 21, wherein the first movable member takes the form of an open housing in which the second movable member is at least partially accommodated, the housing having at least first and second internal surfaces which limit movement of the second movable member.

23. A fixator according to claim 21, wherein at least one of said pins is located in a slot, which serves to limit movement of the movable members.

* * * * *